United States Patent
Barde et al.

(10) Patent No.: US 9,265,754 B2
(45) Date of Patent: Feb. 23, 2016

(54) USE OF 1-{4-[1-(4-CYCLOHEXYL-3-TRIFLUORO-METHYL-BENZYLOXYIMINO)-ETHYL]-2-ETHYL-BENZYL}-AZETIDINE-3-CARBOXYLIC ACID IN TREATING SYMPTOMS ASSOCIATED WITH RETT SYNDROME

(71) Applicants: Yves-Alain Barde, Basel (CH); Graeme Bilbe, Neuchâtel (CH); Ruben Deogracias, Basel (CH); Rainer R. Kuhn, Riehen (CH); Tomoya Matsumoto, Basel (CH); Anis Khusro Mir, Bartenheim (FR); Anna Svenja Schubart, Basel (CH)

(72) Inventors: Yves-Alain Barde, Basel (CH); Graeme Bilbe, Neuchâtel (CH); Ruben Deogracias, Basel (CH); Rainer R. Kuhn, Riehen (CH); Tomoya Matsumoto, Basel (CH); Anis Khusro Mir, Bartenheim (FR); Anna Svenja Schubart, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/097,623

(22) Filed: Dec. 5, 2013

(65) Prior Publication Data

US 2014/0235610 A1 Aug. 21, 2014

Related U.S. Application Data

(60) Continuation of application No. 13/310,941, filed on Dec. 5, 2011, now abandoned, which is a division of application No. 12/598,771, filed as application No. PCT/EP2008/055405 on May 1, 2008, now abandoned.

(60) Provisional application No. 60/915,985, filed on May 4, 2007.

(51) Int. Cl.
| | |
|---|---|
| *A61K 31/397* | (2006.01) |
| *A61K 31/138* | (2006.01) |
| *A61K 31/145* | (2006.01) |
| *A61K 31/137* | (2006.01) |
| *A61K 45/06* | (2006.01) |

(52) U.S. Cl.
CPC ............ *A61K 31/397* (2013.01); *A61K 31/137* (2013.01); *A61K 31/138* (2013.01); *A61K 31/145* (2013.01); *A61K 45/06* (2013.01)

(58) Field of Classification Search
CPC .. A61K 31/397; A61K 31/145; A61K 31/138
See application file for complete search history.

(56) References Cited

U.S. PATENT DOCUMENTS

| | | |
|---|---|---|
| 2005/0043534 A1 | 2/2005 | Bielawska et al. |
| 2014/0011884 A1* | 1/2014 | Barde et al. ................... 514/653 |

FOREIGN PATENT DOCUMENTS

| | | |
|---|---|---|
| WO | 03029205 | 4/2003 |
| WO | 03062252 | 7/2003 |
| WO | 2004103306 | 12/2004 |
| WO | 2005025553 | 3/2005 |
| WO | 2005041899 | 5/2005 |

(Continued)

OTHER PUBLICATIONS

National Institute for Neurological Disorders and Stroke (NINDS), "Rett Syndrome Fact Sheet," Electronic Resource: https://ninds.nih.gov/disorders/rett/detail_rett.htm, retrieved on Oct. 2, 2009.*

(Continued)

*Primary Examiner* — Anna Pagonakis
(74) *Attorney, Agent, or Firm* — James Lynch

(57) ABSTRACT

Use of an S1P receptor modulator in the treatment or prevention of a disease or condition dependent on brain-derived neurotrophic factor (BDNF) expression.

3 Claims, 5 Drawing Sheets

(56) References Cited

FOREIGN PATENT DOCUMENTS

| WO | 2005105146 | 11/2005 |
|---|---|---|
| WO | 2006058316 | 6/2006 |
| WO | 2006064616 | 6/2006 |
| WO | 2006094705 | 9/2006 |

OTHER PUBLICATIONS

UPMC, "Rett Syndrome," Electronic Resource: http://www.upmc.com/HealthAtoZ/Pages/HealthLibrary.aspx?chunkiid=22489, retrieved on Oct. 2, 2009.*

Jope et al., 2006, Glycogen synthase kinase-3 (GSK3) in psychiatric diseases and therapeutic interventions. Curr. Drug Targets.Nov. 2006;7 (11 ): 1421-1434 [found Dec. 17, 2012] (found in database PMC ncbi.nlm.nih.gov/PMC) A§CREB and BDNF.

Bayes M. Gateways to clinical trials. Methods Find.Exp.Ciin. Pharmacol.Mar. 2007;29(2): 153-73 Abstract [online] [found Dec. 18, 2012] (found in database PubMed PMID: 8883822).

Rouillon F. et al. [Pharmaco-epidemiologic study of the use of antidepressant drugs in the general population], Encephale.May 1996; 22 Spec No. 1:39-48 Abstract [online] [found Dec. 18, 2012](found in database PubMed, PMID:8767026).

Jelinsky et al., "Factors associated with depression in patients referred to headache specialists," Neurology, Feb. 2007, 13:68(7): 489-495.

Razavi et al. TRPV1 +sensory neurons control beta cell stress and islet inflammation in autoimmune diabetes. (Cell, 127, 1123-1125, Dec. 15, 2006).

Depression (major depression). Retrieved on Feb. 21, 2013. Electronic Resource: [http://www. mayocl in ic.com/health/depression/DSOO 175/M ETHOD=print& OS ECTION=all].

America. The efficacy of vitamins for reducing or preventing depression symptoms in healthy individuals: natural remedy or placebo? J. Behay. Med. 2008,31: 157-167.

Kowatch et al. Combination pharmacotherapy in children and adolescents with bipolar disorder. Bioi. Psychiatry, 2003; 53: 978-984.

Kasselman et al. BDNF:a missing link between sympathetic dysfunction and inflammatory disease? Journal of Neuroimmunology, 175, 2006, 118-127.

Monaco III et al., Frontiers in Bioscience, vol. 10, pp. 143-159 (Jan. 1, 2005).

J Neurol Neurosurg Ps~chiat[Y. Oct. 1980;43(10):861-5.

Diem, 2007, Journal of Neuroimmunology, 184: 27-36.

Yang, Z et al (2003) Clinical Immunology 107: 30-35.

Maki, T et al (2002) Transplantation 74: 1684-1686.

Chang, Q, et at; "The disease progression of Mecp2 Mutant mice is affected by the level of BDNF expression", Neuron 49(3), 2006, pp. 341-348.

* cited by examiner

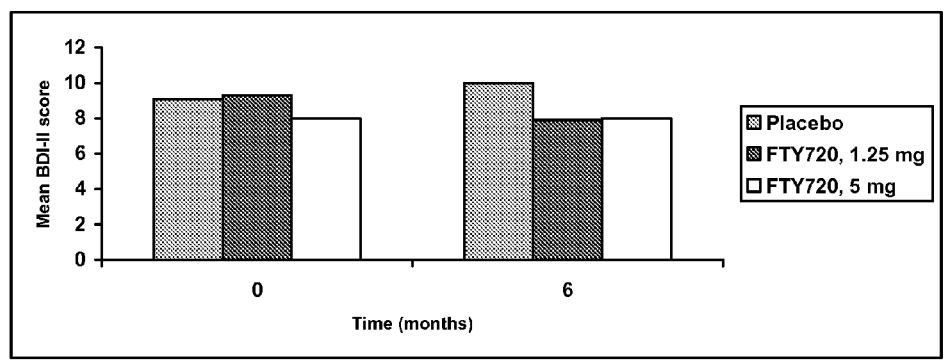
Figure 5. Mean BDI-II scores during the core study.
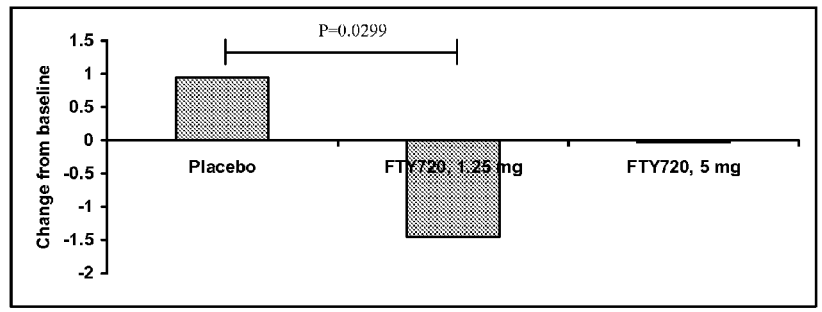
Figure 6. Changes in BDI-II scores from baseline during the core study.

USE OF 1-{4-[1-(4-CYCLOHEXYL-3-TRIFLUORO-METHYL-BENZYLOXYIMINO)-ETHYL]-2-ETHYL-BENZYL}-AZETIDINE-3-CARBOXYLIC ACID IN TREATING SYMPTOMS ASSOCIATED WITH RETT SYNDROME

CROSS REFERENCE TO RELATED APPLICATIONS

This application is a divisional application of U.S. patent application Ser. No. 13/310,941, filed Dec. 5, 2011, which is a divisional of U.S. patent application Ser. No. 12/598,771, filed Nov. 4, 2009, now abandoned, which is a national stage application of PCT/EP2008/055405, filed May 1, 2008, which claims priority to U.S. Pat. App. No. 60/915,985, filed May 4, 2007.

FIELD OF THE INVENTION

The present invention relates to the use of an S1P receptor modulator in the treatment or prevention of a peripheral nervous system disorder, such as Guillan Barre syndrome (GBS)

BACKGROUND OF THE DISCLOSURE

One of the neurotrophic factors, a brain-derived neurotrophic factor (hereinafter, often referred to as BDNF), is a protein, which is provided from target cells or neurons and glial cells and Schwann cells in the living body, and shows activities to maintain the survival and differentiation of neurons.

SUMMARY OF THE INVENTION

It has now been surprisingly shown that S1P receptor modulators can induce BDNF production.

BDNF has been known as a therapeutic agent for treatment of neurodegenerative diseases (e.g., ALS) or diabetic peripheral neuropathy. BDNF has also been described to be useful as a therapeutic agent for treatment of diabetic mellitus.

Therefore, by inducing BDNF production (or stimulating BDNF expression) S1P receptor modulators can be employed to treat such conditions affected by BDNF, i.e. conditions which can be treated, delayed or prevented by the increased expression of BDNF.

BRIEF DESCRIPTION OF THE DRAWINGS

FIG. 5 shows the mean BDI-II (Beck Depression Inventory, second edition) scores of patients participating in a 6 month, placebo controlled Phase II trial of FTY720 in 281 patients having relapsing multiple sclerosis, at the beginning and end of such study (i.e., at t=0 months and t=6 months).

FIG. 6 shows the changes from baseline in the BDI-II scores of the 281 patients in the study referred to above in the description of FIG. 5.

DETAILED DESCRIPTION OF THE INVENTION

Figure 1:
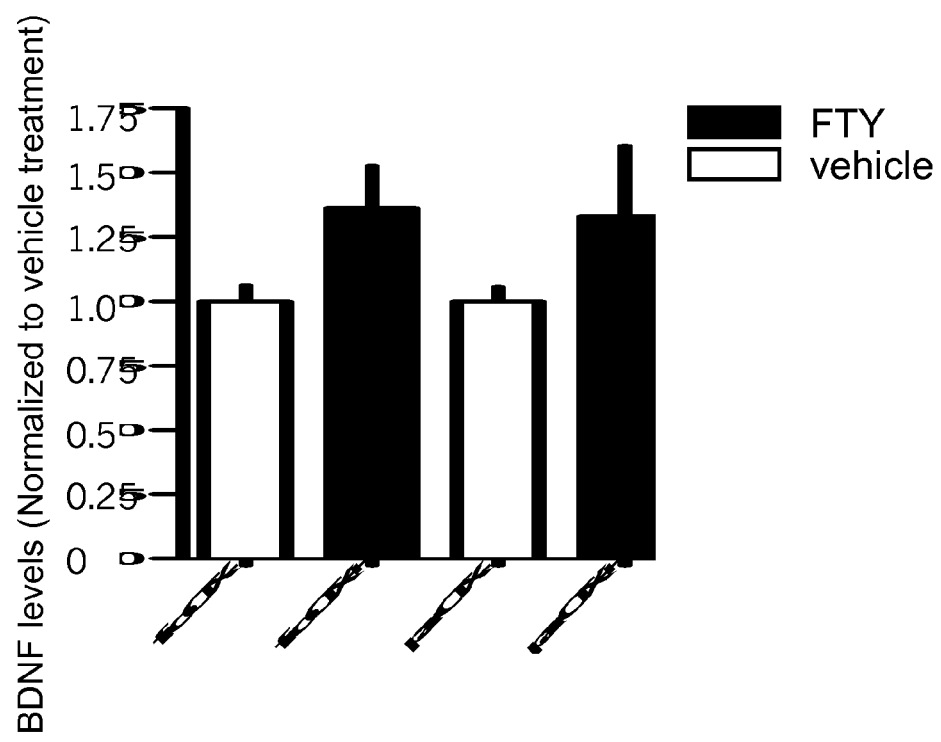
FIG. 1 shows the induction of BDNF in the cortex of female DA rats after a 9-day treatment period with 0.3 mg/kg/d FTY720 measured by Western blot. Shown on the y-axis is the relative intensity of BDNF signal of animals treated with FTY720 vs control animals that had received vehicle (i.e., ratio of signal from FTY720-treated rats divided by signal from vehicle-treated rats, n=3 rats/group). On the x axis, the first two bars come from the frontal cortex, the second two from the parietal cortex and in each case the white bar represents the vehicle treated animals and the black bar represents the FTY720 treated animals.

S1P receptor modulators are typically sphingosine analogues, such as 2-substituted 2-amino-propane-1,3-diol or 2-amino-propanol derivatives, e.g. a compound comprising a group of formula Y.

Sphingosine-1 phosphate (hereinafter "S1P") is a natural serum lipid. Presently there are eight known S1P receptors, namely S1P1 to S1P8. S1P receptor modulators are typically sphingosine analogues, such as 2-substituted 2-amino-propane-1,3-diol or 2-amino-propanol derivatives, e.g. a compound comprising a group of formula Y

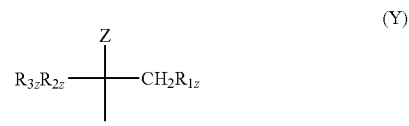

(Y)

wherein Z is H, $C_{1-6}$alkyl, $C_{2-6}$alkenyl, $C_{2-6}$alkynyl, phenyl, phenyl substituted by OH, $C_{1-6}$alkyl substituted by 1 to 3 substituents selected from the group consisting of halogen, $C_{3-8}$cycloalkyl, phenyl and phenyl substituted by OH, or $CH_2$—$R_{4z}$ wherein $R_{4z}$ is OH, acyloxy or a residue of formula (a)

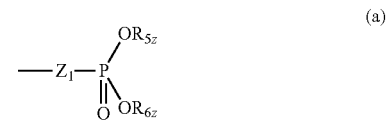

(a)

wherein $Z_1$ is a direct bond or O, preferably O;
each of $R_{5z}$ and $R_{6z}$, independently, is H, or $C_{1-4}$alkyl optionally substituted by 1, 2 or 3 halogen atoms;
$R_{1z}$ is OH, acyloxy or a residue of formula (a); and each of $R_{2z}$ and $R_{3z}$ independently, is H, $C_{1-4}$alkyl or acyl.

Group of formula Y is a functional group attached as a terminal group to a moiety which may be hydrophilic or lipophilic and comprise one or more aliphatic, alicyclic, aromatic and/or heterocyclic residues, to the extent that the resulting molecule wherein at least one of Z and $R_{1z}$ is or comprises a residue of formula (a), signals as an agonist at one or more sphingosine-1-phosphate receptor.

S1P receptor modulators are compounds which signal as agonists at one or more sphingosine-1 phosphate receptors, e.g. S1P1 to S1P8. Agonist binding to a S1P receptor may e.g. result in dissociation of intracellular heterotrimeric G-proteins into Gα-GTP and Gβγ-GTP, and/or increased phosphorylation of the agonist-occupied receptor and activation of downstream signaling pathways/kinases.

The binding affinity of S1P receptor modulators to individual human S1P receptors may be determined in following assay:

S1P receptor modulator activities of compounds are tested on the human S1P receptors $S1P_1$, $S1P_2$, $S1P_3$, $S1P_4$ and $S1P_5$. Functional receptor activation is assessed by quantifying compound induced GTP [$\gamma$-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-bead (Amersham-Pharmacia) immobilised S1P receptor expressing membrane protein (10-20 μg/well) in the presence of 50 mM Hepes, 100 mM NaCl, 10 mM $MgCl_2$, 10 μM GDP, 0.1% fat free BSA and 0.2 nM GTP [$\gamma$-$^{35}$S] (1200 Ci/mmol). After incubation in 96 well microtiterplates at RT for 120 min, unbound GTP [$\gamma$-$^{35}$S] is separated by a centrifugation step. Luminescence of SPA beads triggered by membrane bound GTP [$\gamma$-$^{35}$S] is quantified with a TOPcount plate reader (Packard). $EC_{50}$s are calculated using standard curve fitting software. In this assay, the S1P
receptor modulators preferably have a binding affinity to S1P receptor <50 nM.

Preferred S1P receptor modulators are e.g. compounds which in addition to their S1P binding properties also have accelerating lymphocyte homing properties, e.g. compounds which elicit a lymphopenia resulting from a re-distribution, preferably reversible, of lymphocytes from circulation to secondary lymphatic tissue, without evoking a generalized immunosuppression. Naïve cells are sequestered; CD4 and CD8 T-cells and B-cells from the blood are stimulated to migrate into lymph nodes (LN) and Peyer's patches (PP).

The lymphocyte homing property may be measured in following Blood Lymphocyte Depletion assay:

A S1P receptor modulator or the vehicle is administered orally by gavage to rats. Tail blood for hematological monitoring is obtained on day 1 to give the baseline individual values, and at 2, 6, 24, 48 and 72 hours after application. In this assay, the S1P receptor agonist or modulator depletes peripheral blood lymphocytes, e.g. by 50%, when administered at a dose of e.g. <20 mg/kg.

Examples of appropriate S1P receptor modulators are, for example:
Amino Alcohol Compounds of Formula I

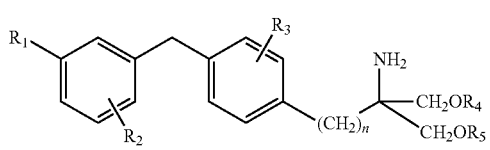

wherein X is O, S, SO or $SO_2$;
$R_1$ is halogen, trihalomethyl, OH, $C_{1-7}$alkyl, $C_{1-4}$alkoxy, trifluoromethoxy, phenoxy, cyclohexylmethyloxy, pyridylmethoxy, cinnamyloxy, naphthylmethoxy, phenoxymethyl, $CH_2$—OH, $CH_2$—$CH_2$—OH, $C_{1-4}$alkylthio, $C_{1-4}$alkylsulfinyl, $C_{1-4}$alkylsulfonyl, benzylthio, acetyl, nitro or cyano, or phenyl, phenyl$C_{1-4}$alkyl or phenyl-$C_{1-4}$alkoxy each phenyl group thereof being optionally substituted by halogen, $CF_3$, $C_{1-4}$alkyl or $C_{1-4}$alkoxy;

$R_2$ is H, halogen, trihalomethyl, $C_{1-4}$alkoxy, $C_{1-7}$alkyl, phenethyl or benzyloxy;
$R_3$ H, halogen, $CF_3$, OH, $C_{1-7}$alkyl, $C_{1-4}$alkoxy, benzyloxy, phenyl or $C_{1-4}$alkoxymethyl;
each of $R_4$ and $R_5$, independently is H or a residue of formula (a)

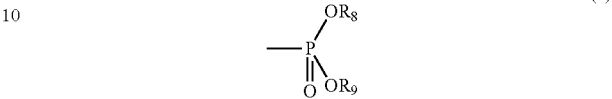

wherein each of $R_8$ and $R_9$, independently, is H or $C_{1-4}$alkyl optionally substituted by halogen; and
n is an integer from 1 to 4;
or a pharmaceutically acceptable salt thereof;
or a compound of formula II

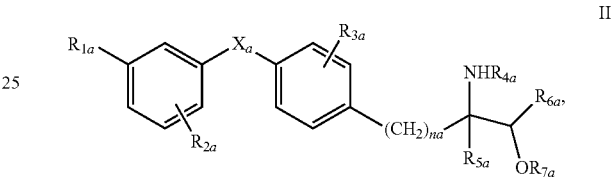

wherein
$R_{1a}$ is halogen, trihalomethyl, $C_{1-4}$alkyl, $C_{1-4}$alkoxy, $C_{1-4}$alkylthio, $C_{1-4}$alkylsulifinyl, $C_{1-4}$alkylsulfonyl, aralkyl, optionally substituted phenoxy or aralkyloxy;
$R_{2a}$ is H, halogen, trihalomethyl, $C_{1-4}$alkyl, $C_{1-4}$alkoxy, aralkyl or aralkyloxy;
$R_{3a}$ is H, halogen, $CF_3$, $C_{1-4}$alkyl, $C_{1-4}$alkoxy, $C_{1-4}$alkylthio or benzyloxy;
$R_{4a}$ is H, $C_{1-4}$alkyl, phenyl, optionally substituted benzyl or benzoyl, or lower aliphatic $C_{1-5}$acyl;
$R_{5a}$ is H, monohalomethyl, $C_{1-4}$alkyl, $C_{1-4}$alkoxy-methyl, $C_{1-4}$alkyl-thiomethyl, hydroxyethyl, hydroxypropyl, phenyl, aralkyl, $C_{2-4}$alkenyl or -alkynyl;
$R_{6a}$ is H or $C_{1-4}$alkyl;
$R_{7a}$ is H, $C_{1-4}$alkyl or a residue of formula (a) as defined above,
$X_a$ is O, S, SO or $SO_2$; and
$n_a$ is an integer of 1 to 4;
or a pharmaceutically acceptable salt thereof.

With regard to the compounds of formulae (I) and (II), the term "halogen" encompasses fluorine, chlorine, bromine and iodine. The term "trihalomethyl group" encompasses trifluoromethyl and trichloromethyl. "$C_{1-7}$alkyl" encompasses straight-chained or branched alkyl, e.g. methyl, ethyl, propyl, isopropyl, butyl, t-butyl, pentyl, hexyl or heptyl. The phrase "substituted or unsubstituted phenoxy group" encompasses those that have, at any position of its benzene ring, a halogen atom, such as fluorine, chlorine, bromine and iodine, trifluoromethyl, $C_{1-4}$alkyl or $C_{1-4}$alkoxy. The term "aralkyl group" as in "aralkyl group" or "aralkyloxy group" encompasses benzyl, diphenylmethyl, phenethyl and phenylpropyl. Any alkyl moiety as present in "$C_{1-4}$alkoxy", "$C_{1-4}$alkylthio", "$C_{1-4}$alkylsulfinyl" or "$C_{1-4}$alkylsulfonyl encompasses straight-chained or branched $C_{1-4}$alkyl, e.g. methyl, ethyl, propyl, isopropyl or butyl. The phrase "substituted or unsubstituted aralkyl group" encompasses those that have, at any position of its benzene ring, a halogen atom, such as fluorine, chlorine, bromine and iodine, trifluoromethyl, lower alkyl having 1-4 carbon atoms, or lower alkoxy having 1-4 carbon atoms.

Other compounds of formula I are compounds of formula Ia

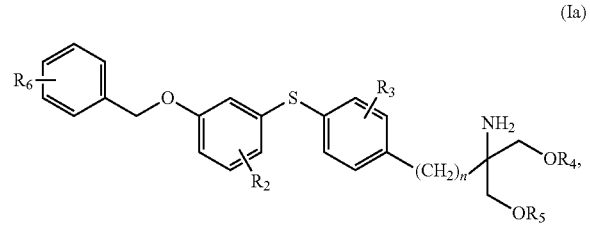

wherein
$R_2$, $R_3$, $R_4$, $R_5$ and n are as defined above; and
$R_6$ is hydrogen, halogen, $C_{1-7}$alkyl, $C_{1-4}$alkoxy or trifluoromethyl.

Further preferred compounds of formula (Ia) are those wherein $R_3$ is chlorine, e.g., 2-amino-2-[4-(3-benzyloxyphenylthio)-2-chlorophenyl]-2-ethyl-propane-1,3-diol, 2-amino-2-[4-(3-benzyloxyphenoxy)-2-chlorophenyl]propyl-1,3-propane-diol or 2-amino-2-[4-(3-benzyloxyphenylthio)-2-chlorophenyl]propyl-1,3-propane-diol or a pharmacological salts or hydrates thereof and theirs corresponding phosphate derivatives. Also exemplified is phosphoric acid mono-2-amino-2-[4-(3-benzyloxyphenylthio)-2-chlorophenyl]ethyl-propyl]ester. The phosphoric acid mono-2-amino-2-[4-(3-benzyloxyphenylthio)-2-chlorophenyl]ethyl-propyl]ester can be prepared enantiomerically pure by the procedures described in WO 2005/021503.

Other compounds of formula II are compounds of formula (IIa)

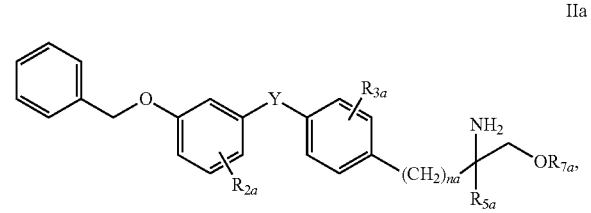

wherein
Y is O or S; and
$R_{2a}$, $R_{3a}$, $R_{5a}$, $R_{7a}$ and $n_a$ are as defined above.

Preferred compounds of formula (IIa) are those wherein $R_3$ is chlorine, e.g., 2-amino-4-[4-(3-benzyloxyphenylthio)-2-chlorophenyl]-2-methylbutane-1-ol; the corresponding phosphoric acid mono-2-amino-4-[4-(3-benzyloxyphenylthio)-2-chlorophenyl]-2-methylbutyl]ester; 2-amino-4-[4-(3-benzyloxyphenylthio)-2-chlorophenyl]-2-ethylbutane-1-ol; and the corresponding phosphoric acid mono-2-amino-4-[4-(3-benzyloxyphenylthio)-2-chlorophenyl]-2-ethylbutyl]ester.

Compounds of formulae I and II are known and are disclosed e.g. in WO03/029205, WO 03/029184 and WO04/026817, respectively, the phosphorylated derivatives being disclosed e.g. in WO04/074297, the contents of which being incorporated herein by reference in their entirety. Compounds of formulae I and II may be prepared as disclosed in above cited references.

Phosphorylated derivatives of compounds of formula (I), e.g., phosphoric acid mono-2-amino-2-[4-(3-benzyloxyphenylthio)-2-chlorophenyl]ethyl-propyl]ester, can be prepared utilizing the procedures for synthesizing phosphorylated compounds described e.g., in WO 2005/021503 (see, e.g., pages 11 and 12). Optically active compounds of structural formula (I) and phosphorylated derivatives thereof, in particular of formula (Ia) can be prepared in high purity utilizing the procedure described, e.g., in Hinterding et al., *Synthesis*, Vol. 11, pp. 1667-1670 (2003). As an example, an optically active compound of structural formula (Ia), phosphoric acid mono-2-amino-2-[4-(3-benzyloxyphenylthio)-2-chlorophenyl]ethyl-propyl]ester, can be prepared as described in the scheme below utilizing the procedures of Hinterding et al. (2003) supra.

Also included are compounds as disclosed in EP627406A1, e.g. a compound of formula III

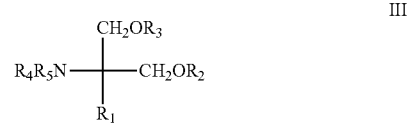

wherein $R_1$ is a straight- or branched $(C_{12-22})$ chain
which may have in the chain a bond or a hetero atom selected from a double bond, a triple bond, O, S, $NR_6$, wherein $R_6$ is H, $C_{1-4}$alkyl, aryl-$C_{1-4}$alkyl, acyl or $(C_{1-4}$alkoxy)carbonyl, and carbonyl, and/or
which may have as a substituent $C_{1-4}$alkoxy, $C_{2-4}$alkenyloxy, $C_{2-4}$alkynyloxy, aryl$C_{1-4}$alkyl-oxy, acyl, $C_{1-4}$alkylamino, $C_{1-4}$alkylthio, acylamino, $(C_{1-4}$alkoxy)carbonyl, $(C_{1-4}$alkoxy)-carbonylamino, acyloxy, $(C_{1-4}$alkyl)carbamoyl, nitro, halogen, amino, hydroxyimino, hydroxy or carboxy; or $R_1$ is
a phenylalkyl wherein alkyl is a straight- or branched $(C_{6-20})$carbon chain; or
a phenylalkyl wherein alkyl is a straight- or branched $(C_{1-30})$carbon chain wherein said phenylalkyl is substituted by
a straight- or branched $(C_{6-20})$carbon chain optionally substituted by halogen,
a straight- or branched $(C_{6-20})$alkoxy chain optionally substituted by halogen,
a straight- or branched $(C_{6-20})$alkenyloxy,
phenyl-$C_{1-14}$alkoxy, halophenyl-$C_{1-14}$alkoxy, phenyl-$C_{1-14}$alkoxy-$C_{1-14}$alkyl, phenoxy-$C_{1-4}$alkoxy or phenoxy-$C_{1-4}$alkyl,
cycloalkylalkyl substituted by $C_{6-20}$alkyl,
heteroarylalkyl substituted by $C_{6-20}$alkyl,
heterocyclic $C_{6-20}$ alkyl or
heterocyclic alkyl substituted by $C_{2-20}$alkyl,
and wherein
the alkyl moiety may have
in the carbon chain, a bond or a heteroatom selected from a double bond, a triple bond, O, S, sulfinyl, sulfonyl, or $NR_6$, wherein $R_6$ is as defined above, and
as a substituent $C_{1-4}$alkoxy, $C_{2-4}$alkenyloxy, $C_{2-4}$alkynyloxy, aryl$C_{1-4}$alkyloxy, acyl, $C_{1-4}$alkylamino, $C_{1-4}$alkylthio, acylamino, $(C_{1-4}$alkoxy)carbonyl, $(C_{1-4}$alkoxy)carbonylamino, acyloxy, $(C_{1-4}$alkyl)carbamoyl, nitro, halogen, amino, hydroxy or carboxy, and
each of $R_2$, $R_3$, $R_4$ and $R_5$, independently, is H, $C_{1-4}$ alkyl or acyl or a pharmaceutically acceptable salt or hydrate thereof;

Compounds as disclosed in EP 1002792A1, e.g. a compound of formula IV

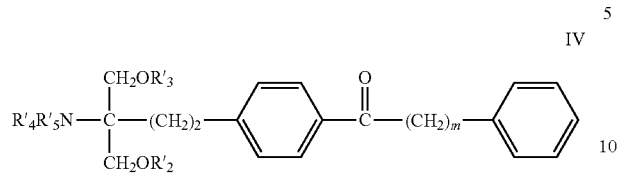

wherein m is 1 to 9 and each of $R'_2$, $R'_3$, $R'_4$ and $R'_5$, independently, is H, $C_{1-6}$alkyl or acyl,
or a pharmaceutically acceptable salt or hydrate thereof;

Compounds as disclosed in EP0778263 A1, e.g. a compound of formula V

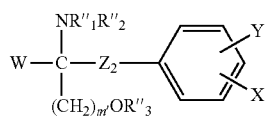

wherein W is H; $C_{1-6}$alkyl, $C_{2-6}$alkenyl or $C_{2-6}$alkynyl; unsubstituted or by OH substituted phenyl;
$R''_4O(CH_2)_n$; or $C_{1-6}$alkyl substituted by 1 to 3 substituents selected from the group consisting of halogen, $C_{3-8}$cycloalkyl, phenyl and phenyl substituted by OH;
X is H or unsubstituted or substituted straight chain alkyl having a number p of carbon atoms or unsubstituted or substituted straight chain alkoxy having a number (p–1) of carbon atoms, e.g. substituted by 1 to 3 substitutents selected from the group consisting of $C_{1-6}$alkyl, OH, $C_{1-6}$alkoxy, acyloxy, amino, $C_{1-6}$alkylamino, acylamino, oxo, halo$C_{1-6}$alkyl, halogen, unsubstituted phenyl and phenyl substituted by 1 to 3 substituents selected from the group consisting of $C_{1-6}$alkyl, OH, $C_{1-6}$alkoxy, acyl, acyloxy, amino, $C_{1-6}$alkylamino, acylamino, halo$C_{1-6}$alkyl and halogen; Y is H, $C_{1-6}$alkyl, OH, $C_{1-6}$alkoxy, acyl, acyloxy, amino, $C_{1-6}$alkylamino, acylamino, halo$C_{1-6}$alkyl or halogen, $Z_2$ is a single bond or a straight chain alkylene having a number or carbon atoms of q, each of p and q, independently, is an integer of 1 to 20, with the proviso of 6≤p+q≤23, m' is 1, 2 or 3, n is 2 or 3, each of $R''_1$, $R''_2$, $R''_3$ and $R''_4$, independently, is H, $C_{1-4}$alkyl or acyl,
or a pharmaceutically acceptable salt or hydrate thereof, Compounds as disclosed in WO02/18395, e.g. a compound of formula VIa or VIb

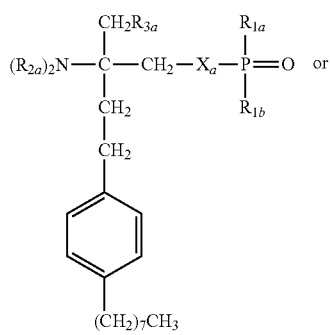

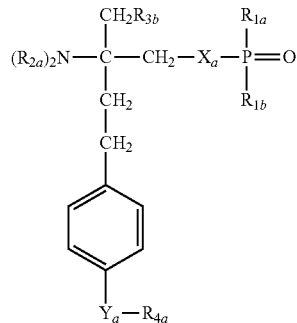

wherein $X_a$ is O, S, $NR_{1s}$ or a group —$(CH_2)_{na}$—, which group is unsubstituted or substituted by 1 to 4 halogen; $n_a$ is 1 or 2, $R_{1s}$ is H or $(C_{1-4})$alkyl, which alkyl is unsubstituted or substituted by halogen; $R_{1a}$ is H, OH, $(C_{1-4})$alkyl or $O(C_{1-4})$alkyl wherein alkyl is unsubstituted or substituted by 1 to 3 halogen; $R_{1b}$ is H, OH or $(C_{1-4})$alkyl, wherein alkyl is unsubstituted or substituted by halogen; each $R_{2a}$ is independently selected from H or $(C_{1-4})$alkyl, which alkyl is unsubstituted or substituted by halogen; $R_{3a}$ is H, OH, halogen or $O(C_{1-4})$alkyl wherein alkyl is unsubstituted or substituted by halogen; and $R_{3b}$ is H, OH, halogen, $(C_{1-4})$alkyl wherein alkyl is unsubstituted or substituted by hydroxy, or $O(C_{1-4})$alkyl wherein alkyl is unsubstituted or substituted by halogen; $Y_a$ is —$CH_2$—, —C(O)—, —CH(OH)—, —C(=NOH)—, O or S, and $R_{4a}$ is $(C_{4-14})$alkyl or $(C_{4-14})$alkenyl;
or a pharmaceutically acceptable salt or hydrate thereof;

Compounds as disclosed in WO02/06268A1, e.g. a compound of formula VII

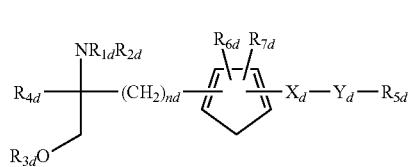

wherein each of $R_{1d}$ and $R_{2d}$, independently, is H or an amino-protecting group;
$R_{3d}$ is hydrogen, a hydroxy-protecting group or a residue of formula

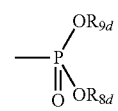

$R_{4d}$ is $C_{1-4}$alkyl;
$n_d$ is an integer of 1 to 6;
$X_d$ is ethylene, vinylene, ethynylene, a group having a formula -D-$CH_2$— (wherein D is carbonyl, —CH(OH)—, O, S or N), aryl or aryl substituted by up to three substitutents selected from group a as defined hereinafter;
$Y_d$ is single bond, $C_{1-10}$alkylene, $C_{1-10}$alkylene which is substituted by up to three substituents selected from groups a and b, $C_{1-10}$alkylene having O or S in the middle or end of the carbon chain, or $C_{1-10}$alkylene having O or S in the middle or end of the carbon chain which is substituted by up to three substituents selected from groups a and b;

$R_{5d}$ is hydrogen, $C_{3-6}$cycloalkyl, aryl, heterocyclic group, $C_{3-6}$cycloalkyl substituted by up to three substituents selected from groups a and b, aryl substituted by up to three substituents selected from groups a and b, or heterocyclic group substituted by up to three substituents selected from groups a and b;

each of $R_{6d}$ and $R_{7d}$, independently, is H or a substituent selected from group a;

each of $R_{8d}$ and $R_{9d}$, independently, is H or $C_{1-4}$alkyl optionally substituted by halogen;

<group a> is halogen, lower alkyl, halogeno lower alkyl, lower alkoxy, lower alkylthio, carboxyl, lower alkoxycarbonyl, hydroxy, lower aliphatic acyl, amino, mono-lower alkylamino, di-$C_{1-4}$alkylamino, acylamino, cyano or nitro; and <group b> is $C_{3-6}$cycloalkyl, aryl or heterocyclic group, each being optionally substituted by up to three substituents selected from group a;

with the proviso that when $R_{5d}$ is hydrogen, $Y_d$ is a either a single bond or linear $C_{1-10}$ alkylene, or a pharmacologically acceptable salt, ester or hydrate thereof;

Compounds as disclosed in JP-14316985 (JP2002316985), e.g. a compound of formula VII

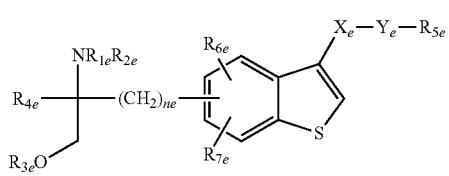

wherein $R_{1e}$, $R_{2e}$, $R_{3e}$, $R_{4e}$, $R_{5e}$, $R_{6e}$, $R_{7e}$, $n_e$, $X_e$ and $Y_e$ are as disclosed in JP-14316985;

or a pharmacologically acceptable salt, ester or hydrate thereof;

Compounds as disclosed in WO03/062252A1, e.g. a compound of formula IX

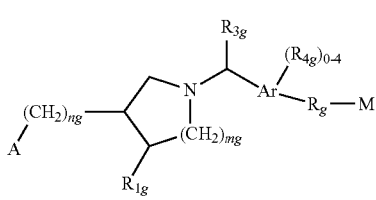

wherein

Ar is phenyl or naphthyl; each of $m_g$ and $n_g$ independently is 0 or 1; A is selected from COOH, $PO_3H_2$, $PO_2H$, $SO_3H$, $PO(C_{1-3}$alkyl)OH and 1H-tetrazol-5-yl; each of $R_{1g}$ and $R_{2g}$ independently is H, halogen, OH, COOH or $C_{1-4}$alkyl optionally substituted by halogen; $R_{3g}$ is H or $C_{1-4}$alkyl optionally substituted by halogen or OH; each $R_{4g}$ independently is halogen, or optionally halogen substituted $C_{1-4}$alkyl or $C_{1-3}$alkoxy; and each of $R_9$ and M has one of the significances as indicated for B and C, respectively, in WO03/062252A1;

or a pharmacologically acceptable salt, solvate or hydrate thereof;

Compounds as disclosed in WO 03/062248A2, e.g. a compound of formula X

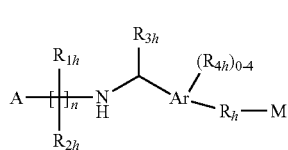

wherein Ar is phenyl or naphthyl; n is 2, 3 or 4; A is COOH, 1H-tetrazol-5-yl, $PO_3H_2$, $PO_2H_2$, —$SO_3H$ or $PO(R_{5h})OH$ wherein $R_{5h}$ is selected from $C_{1-4}$alkyl, hydroxy$C_{1-4}$alkyl, phenyl, —CO—$C_{1-3}$alkoxy and —CH(OH)-phenyl wherein said phenyl or phenyl moiety is optionally substituted; each of $R_{1h}$ and $R_{2h}$ independently is H, halogen, OH, COOH, or optionally halogeno substituted $C_{1-6}$alkyl or phenyl; $R_{3h}$ is H or $C_{1-4}$alkyl optionally substituted by halogen and/OH; each $R_{4h}$ independently is halogen, OH, COOH, $C_{1-4}$alkyl, $S(O)_{0, 1\ or\ 2}C_{1-3}$alkyl, $C_{1-3}$alkoxy, $C_{3-6}$cycloalkoxy, aryl or aralkoxy, wherein the alkyl portions may optionally be substituted by 1-3 halogens; and each of $R_h$ and M has one of the significances as indicated for B and C, respectively, in WO03/062248A2 or a pharmacologically acceptable salt, solvate or hydrate thereof.

Compounds as disclosed in WO 04/103306A, WO 05/000833, WO 05/103309 or WO 05/113330, e.g. compounds of formula XIa or XIb

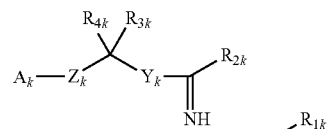

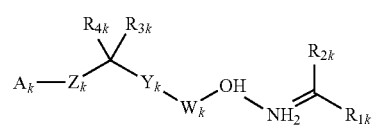

wherein
$A_k$ is $COOR_{5k}$, $OPO(OR_{5k})_2$, $PO(OR_{5k})_2$, $SO_2OR_{5k}$, $POR_{5k}OR_{5k}$ or 1H-tetrazol-5-yl, $R_{5k}$ being H or $C_{1-6}$alkyl;
$W_k$ is a bond, $C_{1-3}$alkylene or $C_{2-3}$alkenylene;
$Y_k$ is $C_{6-10}$aryl or $C_{3-9}$heteroaryl, optionally substituted by 1 to 3 radicals selected from halogene, OH, $NO_2$, $C_{1-6}$alkyl, $C_{1-6}$alkoxy; halo-substituted $C_{1-6}$alkyl and halo-substituted $C_{1-6}$alkoxy;
$Z_k$ is a heterocyclic group as indicated in WO 04/103306A, e.g. azetidine;
$R_{1k}$ is $C_{6-10}$aryl or $C_{3-9}$heteroaryl, optionally substituted by $C_{1-6}$alkyl, $C_{6-10}$aryl, $C_{6-10}$aryl$C_{1-4}$alkyl, $C_{3-9}$heteroaryl, $C_{3-9}$heteroaryl$C_{1-4}$alkyl, $C_{3-8}$cycloalkyl, $C_{3-8}$cycloalkyl$C_{1-4}$alkyl, $C_{3-8}$heterocycloalkyl or $C_{3-8}$heterocycloalkyl$C_{1-4}$alkyl; wherein any aryl, heteroaryl, cycloalkyl or heterocycloalkyl of $R_{1k}$ may be substituted by 1 to 5 groups selected from halogen, $C_{1-6}$alkyl, $C_{1-6}$alkoxy and halo substituted-$C_{1-6}$alkyl or —$C_{1-6}$alkoxy;
$R_{2k}$ is H, $C_{1-6}$alkyl, halo substituted $C_{1-6}$alkyl, $C_{2-6}$alkenyl or $C_{2-6}$alkynyl: and
each of $R_{3k}$ or $R_{4k}$, independently, is H, halogen, OH, $C_{1-6}$alkyl, $C_{1-6}$alkoxy or halo substituted $C_{1-6}$alkyl or $C_{1-6}$alkoxy;
and the N-oxide derivatives thereof or prodrugs thereof, or a pharmacologically acceptable salt, solvate or hydrate thereof.

The compounds of formulae III to XIb may exist in free or salt form. Examples of pharmaceutically acceptable salts of the compounds of the formulae III to VIII include salts with inorganic acids, such as hydrochloride, hydrobromide and sulfate, salts with organic acids, such as acetate, fumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. The compounds and salts of the combination of the present invention encompass hydrate and solvate forms.

Acyl as indicated above may be a residue $R_y$—CO— wherein $R_y$ is $C_{1-6}$alkyl, $C_{3-6}$cycloalkyl, phenyl or phenyl-$C_{1-4}$alkyl. Unless otherwise stated, alkyl, alkoxy, alkenyl or alkynyl may be straight or branched.

Aryl may be phenyl or naphthyl, preferably phenyl.

When in the compounds of formula I the carbon chain as $R_1$ is substituted, it is preferably substituted by halogen, nitro, amino, hydroxy or carboxy. When the carbon chain is interrupted by an optionally substituted phenylene, the carbon chain is preferably unsubstituted. When the phenylene moiety is substituted, it is preferably substituted by halogen, nitro, amino, methoxy, hydroxy or carboxy.

Preferred compounds of formula III are those wherein $R_1$ is $C_{13-20}$alkyl, optionally substituted by nitro, halogen, amino, hydroxy or carboxy, and, more preferably those wherein $R_1$ is phenylalkyl substituted by $C_{6-14}$-alkyl chain optionally substituted by halogen and the alkyl moiety is a $C_{1-6}$alkyl optionally substituted by hydroxy. More preferably, $R_1$ is phenyl-$C_{1-6}$alkyl substituted on the phenyl by a straight or branched, preferably straight, $C_{6-14}$alkyl chain. The $C_{6-14}$alkyl chain may be in ortho, meta or para, preferably in para.

Preferably each of $R_2$ to $R_5$ is H.

In the above formula of VII "heterocyclic group" represents a 5- to 7 membered heterocyclic group having 1 to 3 heteroatoms selected from S, O and N. Examples of such heterocyclic groups include the heteroaryl groups indicated above, and heterocyclic compounds corresponding to partially or completely hydrogenated heteroaryl groups, e.g. furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, tetrahydropyranyl, morpholinyl, thiomorpholinyl, pyrrolidinyl, pyrrolyl, imidazolidinyl, pyrazolidinyl, piperidinyl, piperazinyl, oxazolidinyl, isoxazolidinyl, thiazolidinyl or pyrazolidinyl. Preferred heterocyclic groups are 5- or 6-membered heteroaryl groups and the most preferred heteocyclic group is a morpholinyl, thiomorpholinyl or piperidinyl group.

A preferred compound of formula III is 2-amino-2-tetradecyl-1,3-propanediol. A particularly preferred S1P receptor agonist of formula I is FTY720, i.e. 2-amino-2-[2-(4-octylphenyl)ethyl]propane-1,3-diol in free form or in a pharmaceutically acceptable salt form (referred to hereinafter as Compound A), e.g. the hydrochloride, as shown:

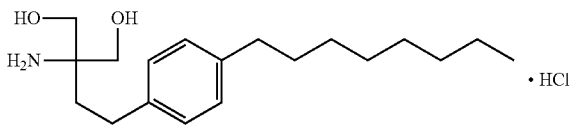 [SMILES: CCCCCCCCc1ccc(CCC(N)(CO)CO)cc1 ; "· HCl"]

A preferred compound of formula IV is the one wherein each of $R'_2$ to $R'_5$ is H and m is 4, i.e. 2-amino-2-{2-[4-(1-oxo-5-phenylpentyl)phenyl]ethyl}propane-1,3-diol, in free form or in pharmaceutically acceptable salt form (referred to hereinafter as Compound B), e.g. the hydrochloride.

A preferred compound of formula V is the one wherein W is $CH_3$, each of $R''_1$ to $R''_3$ is H, $Z_2$ is ethylene, X is heptyloxy and Y is H, i.e. 2-amino-4-(4-heptyloxyphenyl)-2-methylbutanol, in free form or in pharmaceutically acceptable salt form (referred to hereinafter as Compound C), e.g. the hydrochloride. The R-enantiomer is particularly preferred.

A preferred compound of formula VIa is the FTY720-phosphate ($R_{2a}$ is H, $R_{3a}$ is OH, $X_a$ is O, $R_{1a}$ and $R_{1b}$ are OH).

A preferred compound of formula IVb is the Compound C-phosphate ($R_{2a}$ is H, $R_{3b}$ is OH, X, is O, $R_{1a}$ and $R_{1b}$ are OH, $Y_a$ is O and $R_{4a}$ is heptyl). A preferred compound of formula V is Compound B-phosphate.

A preferred compound of formula VIII is (2R)-2-amino-4-[3-(4-cyclohexyloxybutyl)-benzo[b]thien-6-yl]-2-methylbutan-1-ol.

A preferred compound of formula XIa is e.g. 1-{4-[1-(4-cyclohexyl-3-trifluoromethyl-benzyloxyimino)-ethyl]-2-ethyl-benzyl}-azetidine-3-carboxylic acid, or a prodrug thereof.

It will be appreciated that the compounds as described herein may be the direct active substances, or may be prodrugs. For example, the compounds may be phosphorylated forms.

It has now been found that S1P receptor modulators have an inhibitory, preventative or delaying effect on conditions associated with or dependent on or affected by levels of BDNF.

In one particular aspect of the present invention, the compounds as described herein, representing the genus of S1P receptor modulators, increase the levels of BDNF, for example, the compounds as described herein stimulate BDNF production.

A compound which induces brain-derived neurotrophic factor (BDNF) expression can be used as a therapeutic agent for treatment of nervous system disorders and diseases, or treatment of diabetes mellitus.

More particularly, it is useful for nervous system injured by wound, surgery, ischemia, infection, metabolic diseases, malnutrition, malignant tumor, or toxic drug, etc. Especially, it can be used in the treatment of conditions wherein sensory neurons or retinal ganglion cells are injured.

More especially, the compounds can be used in the treatment of congenital conditions or neurodegenerative diseases, for example, Alzheimer's disease, Parkinson's disease (the symptoms of Parkinson's disease may be caused by the degeneration of dopaminergic neuron), Parkinson-Plus syndromes (e.g., progressive spranuclear palsy (Steele-Richardson-Olszewski syndromes), olivopontocerebellar atrophy (OPCA), Shy-Drager syndromes (Multiple Systems Atrophy), and Parkinson dementia complex of Guam), Huntington's disease (Huntington's chorea), and Rett Syndrome, but are not limited thereto.

Further, the compounds can be used in the treatment of sensory nerve dysfunction and congenital diseases or neurodegenerative diseases being associated with degenerative of retina.

In addition, the compounds can be used in the treatment of inherited convulsive paraplegia associated with retina degeneration (Kjellin and Bamard-Scholz syndromes), retinitis pigmentosa, Stargardt disease, Usher syndromes (retinitis pigmentosa accompanied by congenital hearing loss) and Refsum syndrome (retinitis pigmentosa, congenital hearing loss, and polyneuropathy).

Further, the compounds can be used to treat obesity.

The compounds may also be used to treat cognitive impairment and/or attention deficit disorder, for example deficits and abnormalities in attention and vigilance, executive functions and memory (for instance working memory and episodic memory). Other disorders relating to cognitive dysfunction include sleep related breathing disorders (SRBD), behavioral impairments, information processing deficits and age-related disorders, Attention-deficit hyperactivity disorder (ADHD), childhood ADHD, adult ADHD, excess daytime somnolence, sleep apnea, traumatic brain injury, neurodegenerative disorders with associated memory and cognitive problems (such as Alzheimer's disease, Lewy body dementia, senile dementia, vascular dementia, Parkinson's disease), chronic fatigue syndrome, fatigue associated with sleep deprivation or prolonged wakefulness, age-related decline in memory and cognitive function (such as mild cognitive impairment), cognitive impairment associated with mood disorders (such as depression) and anxiety, schizophrenia, day time sleepiness associated with narcolepsy.

In addition, the compounds can be used to treat sleep disorders, e.g. narcolepsy, primary insomnia, sleep-awake rhythm disorders (e.g., work-shift syndrome, time-zone syndrome (jet-lag)).

In additions, the compounds can be used to treat depressive disorder, e.g. manic-depressive psychosis.

In a further use, the compounds can be useful in making patients feel better.

In a series of further specific or alternative embodiments, the present invention provides:
1.1 A method for preventing, inhibiting or treating a condition effected by BDNF production, in a subject in need thereof, comprising administering to said subject a therapeutically effective amount of an S1P receptor modulator, e.g. a compound of formulae I to XIb.
1.2 A method for alleviating or delaying progression of the symptoms of obesity, a sleep disorder or depressive disorder, in a subject in need thereof, in which method the BDNF-dependent factor associated with said disease is prevented or inhibited, comprising administering to said subject a therapeutically effective amount of an S1P receptor modulator, e.g. a compound of formulae I to XIb.
1.3 A method for inducing the production of BDNF, in a subject, comprising administering to said subject a therapeutically effective amount of an S1P receptor modulator, e.g. a compound of formulae I to XIb.
1.4 A method for slowing progression of obesity, a sleep disorder or depressive disorder, in a subject, in which method the BDNF-dependent factor associated with said disease is prevented or inhibited, comprising administering to said subject a therapeutically effective amount of an S1P receptor modulator, e.g. a compound of formulae I to XIb.
1.5 A method as indicated above, wherein the S1P receptor modulator is administered intermittently.
For example, the S1P receptor modulator may be administered to the subject every $2^{nd}$ or $3^{rd}$ day or once a week.
2. A pharmaceutical composition for use in any one of the methods 1.1 to 1.5, comprising an S1P receptor modulator, e.g. a compound of formulae I to XIb as defined hereinabove, together with one or more pharmaceutically acceptable diluents or carriers therefor.
3. An S1P receptor modulator, e.g. a compound of formula I to XIb as defined herein above, for use in any one of the methods 1.1 to 1.5.
4 An S1P receptor modulator, e.g. a compound of formulae I to XIb as defined herein above, for use in the preparation of a medicament for use in any one of the methods 1.1 to 1.5.

Utility of the S1P receptor modulators, e.g. the S1P receptor modulators comprising a group of formula Y, in preventing or treating a disease associated with BDNF as hereinabove specified, may be demonstrated in animal test methods as well as in clinic, for example in accordance with the methods hereinafter described.

EXAMPLE 1

In Vivo: S1P Receptor Modulator Induced BDNF Production

Female DA rats were treated for 9 days (5 days, 2 day pause, 4 days) with FTY720 p.o.
Expt 1: 0.3 mg/kg/d vs. vehicle.
N=3 rats/group
One day after the last treatment, the rats were perfused with ice-cold PBS and different CNS regions were isolated.
The results are shown in FIG. 1.

EXAMPLE 2

In Vivo: S1P Receptor Modulator Induced BDNF Production

Figure 2A:
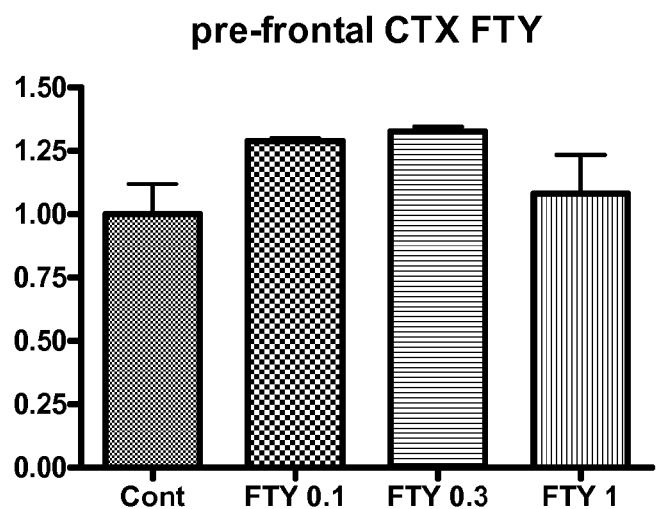
FIGS. 2A-2B: Similar to FIG. 1, FIGS. 2A and 2B show the induction of BDNF in the cortex of female DA rats after a 9-day treatment period, but using multiple doses of FTY720. N=3 animals each were treated with either vehicle, 0.1 mg/kg/d FTY720, 0.3 mg/kg/d FTY720 or 1 mg/kg/d FTY720.
Figure 2B:
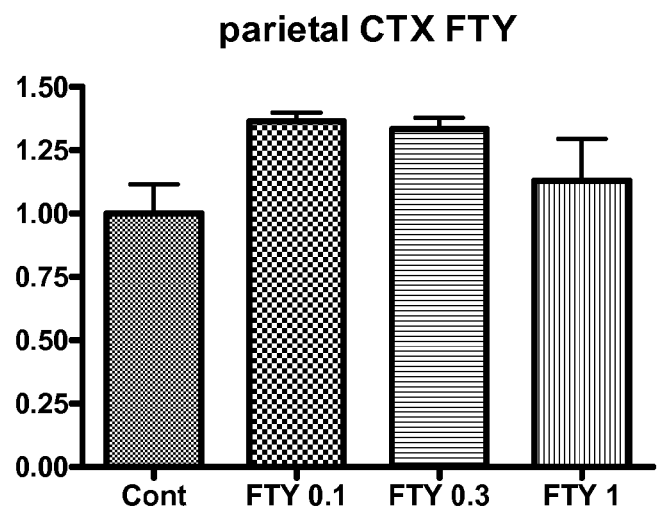

Female DA rats were treated for 9 days (5 days, 2 day pause, 4 days) with FTY720 p.o. 0.1; 0.3 or 1 mg/kg/d vs vehicle
N=3 rats/group
One day after the last treatment, the rats were perfused with ice-cold PBS and different CNS regions were isolated.
The results are shown in FIG. 2.

EXAMPLE 3

In Vitro: S1P Receptor Modulator Induced BDNF Production

Figure 3A:
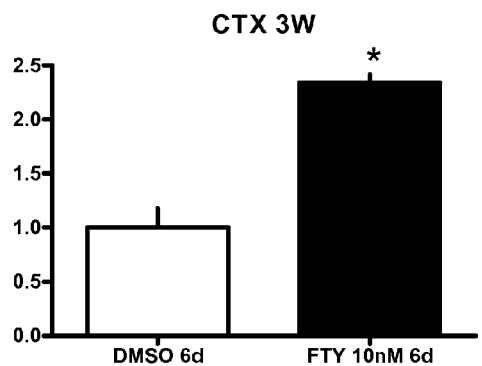
FIG. 3A-3C show the results of a study wherein neuronal cultures were established using neurons from different brain regions. The cells were cultured for a total period of 21 days and FTY720-P was added for the last 6 days of the culture period. As with the results shown in FIGS. 1 and 2, BDNF levels were measured by Western blot and normalised to the level observed in the vehicle control.
Figure 3B:
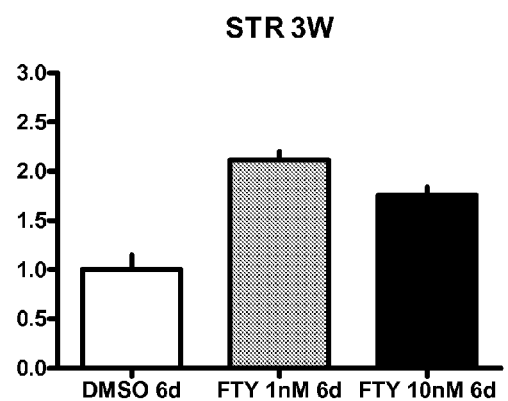
Figure 3C:
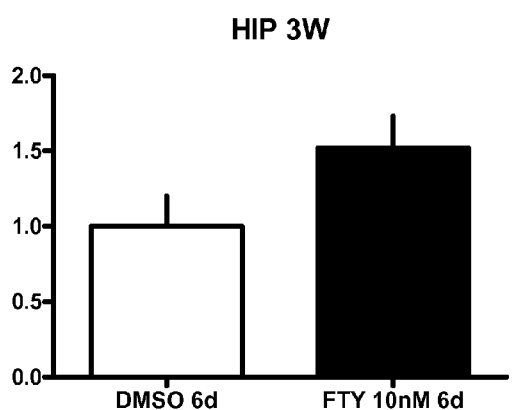

Effect of FTY720 on BDNF expression in cultured CTX, STR, and HIP neurons was investigated.
Neurons were treated with phosphorylated FTY720 (FTY-p) (1 and 10 nM) for the last 6 days.
Cell lysates were collected at 21 days in vitro.
Y axis indicates levels of BDNF normalized to control.
*P<0.05 vs DMSO
The results are shown in FIGS. 3A, B and C.

EXAMPLE 4

In Vitro: S1P Receptor Modulator Induced BDNF Production

Figure 4A:
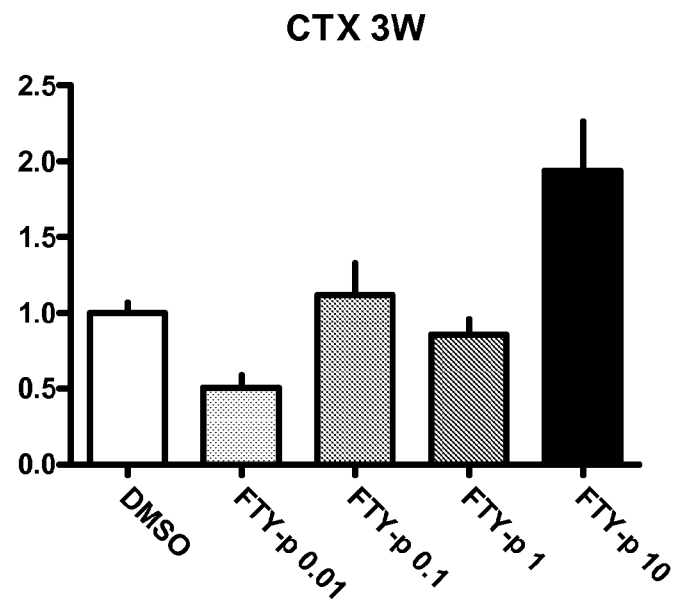
FIG. 4A-4B show the results of a study similar to that shown in FIGS. 3A-C, but using a broader range of concentrations of FTY720P (all in nM).
Figure 4B:
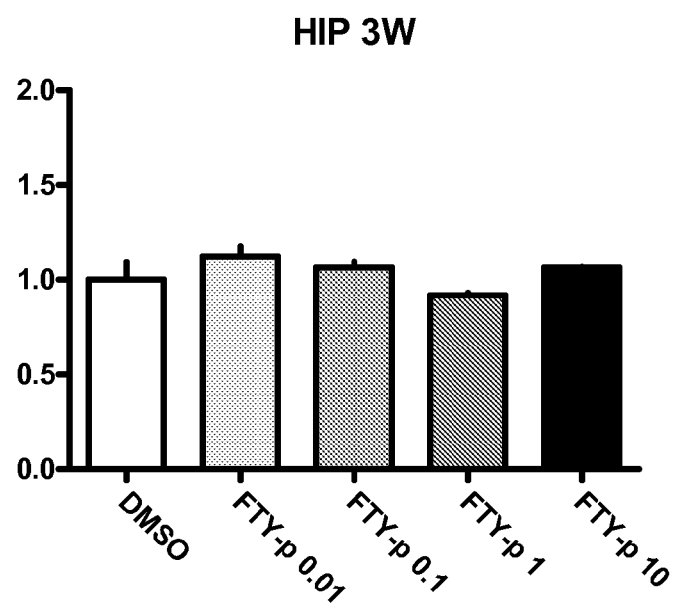

Effect of FTY720 on BDNF expression in cultured CTX and HIP neurons was investigated.
Neurons were treated with FTY720 (FTY-p) (0.01, 0.1, 1 and 10 nM) for the last 6 days.
Cell lysates were collected at 21 days in vitro.
Y axis indicates levels of BDNF normalized to control.
The results are shown in FIG. 4,

EXAMPLE 5

Clinical Trial: S1P Receptor Modulator Made People Feel Better

In a 6-month, placebo controlled, Phase II trial involving 281 patients with relapsing MS, FTY720 reduced gadolinium-enhanced magnetic resonance imaging (MRI) lesions by up to 80%, and the annualized relapse rate by more than 50%, compared with placebo, at doses of 1.25 and 5 mg once daily.[3] The resulting low disease activity on both MRI and relapses was sustained in patients treated with FTY720 for up to 24 months during a dose-blinded extension phase. Patients who received placebo also had marked improvements after switching to FTY720 in the extension.

In this study, depressive symptoms were assessed by means of the Beck Depression Inventory second edition (BDI-II). These results are presented here.

Method

Patients with relapsing MS (relapsing-remitting or secondary progressive) were randomized to receive placebo or FTY720 1.25 or 5 mg/day, for 6 months (the core study). At the end of this period, placebo-treated patients were re-randomized to one of the two FTY720 doses, while those originally randomized to FTY720 continued treatment at the same doses. After approximately 18-24 months, patients receiving FTY720 5 mg, were switched to 1.25 mg in view of evidence that the higher dose conferred no efficacy benefit over the lower dose.

The BDI-II was administered at baseline, and at 3 and 6 months during the core study and at 12 and 24 months during the extension phase (i.e. 6 and 18 months after the start of the extension phase). This is a 21-item self-report scale measuring various symptoms and attitudes associated with depression. Respondents rate depressive symptoms experienced during the past two weeks on a 4-point scale, coded 0 to 3 by increasing order of severity. A total score across all 21 items can be generated, with lower total scores indicating lower overall severity of depressive symptoms. BDI-II total scores of 14 or above are indicative of clinical depression. Ny reduction in the BDI-II score indicated an improvement in depression.

Results

Patients

Of the 281 patients originally randomized to treatment, 255 completed the core study. BDI-II scores at baseline and 6 months were available in 239 patients.

Changes in BDI-II Scores During the Core Study

Mean BDI-II scores during the core study are shown in FIG. 5, and changes in these scores from baseline during the core study are shown in FIG. 6. BDI-II scores decreased from baseline in patients receiving FTY720 1.25 mg/day, remained consistent in patients receiving FTY720 5.0 mg/day, and increased in patients on placebo. At 6 months, the change in BDI-II scores from baseline in FTY720 1.25 mg/day treated patients was significantly greater than in placebo-treated patients. The difference in changes in BDI-II scores between the two doses of FTY720 was not significant at the 5% level.

The invention claimed is:

1. A method for treating one or more symptoms associated with Rett Syndrome, in a subject in need thereof, comprising administering to said subject a therapeutically effective amount of 1-{4-[1-(4-cyclohexyl-3-trifluoromethyl-benzyloxyimino)-ethyl]-2-ethyl-benzyl}-azetidine-3-carboxylic acid.

2. A method according to claim 1, wherein 1-{4-[1-(4-cyclohexyl-3-trifluoromethyl-benzyloxyimino)-ethyl]-2-ethyl-benzyl}-azetidine-3-carboxylic is administered 1 to 3 times per day.

3. A method according to claim 1 comprising co-administration, e.g. concomitantly or in sequence, of a therapeutically effective non-toxic amount of 1-{4-[1-(4-cyclohexyl-3-trifluoromethyl-benzyloxyimino)-ethyl]-2-ethyl-benzyl}-azetidine-3-carboxylic acid and a second therapeutic substance.

* * * * *